United States Patent [19]
Watkins

[11] Patent Number: 5,213,501
[45] Date of Patent: May 25, 1993

[54] MECHANICALLY RETAINED FIXED PARTIAL DENTURE

[76] Inventor: Keith V. Watkins, 18 Chestnut St., Coram, N.Y. 11727

[21] Appl. No.: 804,659

[22] Filed: Dec. 6, 1991

[51] Int. Cl.⁵ .......................................... A61C 13/12
[52] U.S. Cl. .................................... 433/172; 433/182
[58] Field of Search ............... 433/172, 180, 181, 182, 433/183

[56] References Cited

U.S. PATENT DOCUMENTS

| | | | |
|---|---|---|---|
| 1,638,820 | 8/1927 | Baratt | 433/182 |
| 1,941,096 | 12/1933 | Lasky | 433/182 |
| 2,111,787 | 3/1938 | Knowles | 433/172 |
| 2,573,804 | 11/1951 | Neustadter | 433/183 |
| 3,675,326 | 7/1972 | Desmarets | 433/182 |
| 4,406,622 | 9/1983 | Yoon | 433/172 |
| 4,431,415 | 2/1984 | Tigani | 433/172 |
| 4,661,067 | 4/1987 | Harvey, Sr. et al. | 433/180 |
| 4,746,295 | 5/1988 | Kipp | 433/183 |

Primary Examiner—John J. Wilson
Attorney, Agent, or Firm—Charles E. Baxley

[57] ABSTRACT

A mechanically retained fixed partial denture is a three part device which is assembled to form the pontic. The three parts to interlock in a non-displaceable manner as follows: 1) a buccal element engages the buccal surfaces of the abutment teeth 2) a lingual element engages the lingual surfaces of the abutment teeth; 3) part of the buccal element is within the body of the lingual element; 4) and an incisal attachment element then connects the buccal and lingual elements. The incisal attachment element comprises an elongated member which, upon assembly, extends through a linear aperture located within the body of both the buccal element and the lingual element both simultaneously and continuously, to form an interlocking system resulting in one functional unit made up of the three elements. The advantages of this mechanical retention are 1) conservation of tooth structure; 2) efficiency due to time savings; 3) low expense; and 4) no complications of tooth preparation. The devices is adaptable to replace several adjacent teeth.

5 Claims, 3 Drawing Sheets

MECHANICALLY RETAINED FIXED PARTIAL DENTURE

BACKGROUND OF THE INVENTION

1. Field of the Invention

This invention pertains to fixed dental prosthetics, and more particularly, to devices for restoring dentulous spaces in the dentulous arch.

2. Prior Art

One of the most common problems faced in the field of dentistry is loss of teeth. Tooth loss may range in severity from one tooth to all teeth in the mouth. Missing teeth cause problems in speech, chewing, personal appearance, malocclusion, and the temporo-mandibular joint. When a limited number of teeth are missing the restorative options include replacement of the missing teeth with a prosthesis called a fixed partial denture (bridge).

Fixed partial dentures are usually fabricated in the following manner:
- a. The teeth on both sides of the space caused by missing teeth are ground down (prepared).
- b. Impressions are made of these teeth and the space between them.
- c. A metal framework (retainer) is fabricated to fit over the prepared teeth (abutments) with a false tooth (pontic) between the retainers.
- d. Dental porcelain is fused to the metal framework to simulate the appearance and function of natural teeth.
- e. The bridge is permanently cemented onto the prepared teeth. (Dental Clinics of North America 1987, July; 333–346 and 505–528).

This method, though usually successful, does not take into account certain circumstances that would dictate a more conservative approach. For example:
- a. When healthy teeth are prepared for bridges the teeth are more susceptible to decay if the bridge is faulty, or if the bridge becomes loose during function.
- b. This method of bridgework is expensive, precluding its use in certain socioeconomic groups.
- c. The procedure is time consuming, involving many hours of the dentist's time, and the patient must return several times. It may take several weeks to complete.
- d. The procedure usually involves injection of local anesthesia.
- e. Complications of tooth preparation may occur causing pulpal death and then endodontics or even tooth extraction.

Several inventors have addressed these aforementioned problems. U.S. Pat. No. 4,556,388 to Hader discloses a method of fixing dental prostheses with pins and fitted sockets. This method is adaptable to many situations. However, it differs substantially from the devise described herein. The structural components are based upon a sleeve type mechanism, as opposed to retentive elements or the interlock principle.

Another disclosure which furnishes background information is U.S. Pat. No. 4,163,318 in the name of Tigani which discloses a method of restoring edentulous spaces by means of an adjustable device whose central mechanism is a screw. This screw extends arms which engage abutment teeth. This design is novel but does not resemble the invention described herein in all methods of structure or design.

A similar device, with the U.S. Pat. No. 4,431,415 awarded to the same inventor Tiqani, differs from Patent No. 4,163,318 in certain details, but is of the same basic mechanical principle and thus does not resemble in structure or concept the device described herein.

U.S. Pat. No. 3,422,534 to Bahm deviates from the conventional art in that the pontics are mounted upon a sleeve which embraces a bar suspended from the abutment teeth thus filling the space caused by the missing teeth. This design employs abutment teeth that have been prepared in the conventional manner, thus exposing those teeth to the same aforementioned detrimental consequences. The sleeve/bar apparatus serves indeed to support the pontics, but is very dissimilar in concept and design to the system of this invention.

An apparatus of U.S. Pat. No. 3,423,827 awarded to Bahm and Andrews employs similar technology to U.S. Pat. No. 3,422,534 in that the basic principle relates to a bar which supports the pontics. This device also differs conceptually from the invention described herein.

U.S. Pat. No. 4,744,757 to Adair et al. discloses a fixed partial denture which attempts to alleviate problems of error in the conventional art by utilizing crowns resting upon the abutment teeth which have male/female attachments connected to them. These attachments then are joined with a medium cured with visible light radiation. This system again relies upon substantial preparation of the abutment teeth with the attendant problems. The concept and design are very different from the invention described in this application.

U.S. Pat. No. 4,877,400 is based upon a bar extending between abutment teeth which supports a porcelain bridge. This design has laudable goals in terms of esthetics. However, the preparation of the teeth, with the aforementioned problems associated therewith, renders this design inadequate to prevent harmful sequelae to the abutment teeth. The structural design resembles, in no way, the invention described herein.

U.S. Pat. No. 4,950,162 awarded to Korber et al, also utilizes a longitudinal bar which extends between the abutment teeth. The framework can be adjustable and also depends upon substantial preparation of the abutment teeth. Thus the structural concept and design can be seen to be considerably different from the invention proposed herein.

U.S. Pat. No. 5,007,836 to Gayso discloses a method of replacing missing teeth with a groove lock system. There is some utility to this concept but it is limited by its application to replace only one tooth. There are many conceptual and structural differences between this invention and the one proposed herein. For example, there is a one-piece pontic suspended between two teeth, and there are no retentive elements in U.S. Pat. No. 5,007,836. These differences, among others, differentiates the Prior Art from the invention proposed herein.

The Related Art includes an entire class of dental restorations called the Resin-Bonded Retainers. These restorations are successful in limited applications, but there are serious inherent problems in their structural concepts that preclude usage in many applications. The resin-bonded retainers are not advisable in patients with heavy occlusion because of a tendency to dislodge; the resin-bonded retainers are contraindicated on teeth with short clinical crowns; and the teeth must often be prepared in an elaborate fashion to generate a path of insertion. (Dental Clinics of North America, April, 1985, pp. 393-402).

All of the techniques cited, and all those that this inventor is aware of, do not employ the central design concept of the invention described herein. That design concept is the three part device having an interlocking attachment which passes through two opposing and retaining elements simultaneously thus supporting the pontics between the abutment teeth. The Prior Art, and though successful in many instances, still leaves a large number of concerns yet to be adequately addressed. The invention described herein addresses those concerns in the following manner:

a. Regarding the preparation of teeth which leaves the teeth susceptible to decay, the present invention relies upon extremely minimal tooth preparation, which extends only into the enamel. The teeth are thus preserved, for the most part, in their natural anatomical form. The chance for increased rate of decay is thus obviated.

b. The expensive standard method of fabricating fixed partial dentures, precluding its use in many people, is definitely an inadequate feature of that technique. The invention described herein is by far much less expensive for the patient. The technique will allow people with less available income to enjoy the benefits of fixed partial dentures.

c. The invention described herein is far less time consuming to fabricate and insert than the standard methods. It is possible to complete the replacement of many teeth in just one day. The patient's time is saved and the dentist's time is saved.

d. The standard procedures and many of those described in the Prior Art necessitate local anesthetic injections which are uncomfortable for the patient. This invasive procedure also may lead to injury to the patient or the dentist because of the sharpness of the needle. The proposed invention does not require local anesthetic thus precluding such injuries.

e. There are complications associated with tooth preparation in the conventional manner, such as intense heat generated by the high speed dental drill, and inadvertent exposure of the nerve during drilling. Both of these complications are further time consuming, often painful, and expensive. The invention described herein, will not cause either of these complications, because this procedure does not involve extensive grinding of the teeth.

f. The deficiencies in the resin-bonded retainer technique are also overcome with the mechanically retained fixed partial denture. In contrast to the resin-bonded retainer, the mechanically retained fixed partial denture may be used in patients with heavy occlusion, and on teeth with short clinical crowns. The structural concept of this invention which involves engaging the tooth from opposite sides (buccal and lingual) eliminates the need for a path of insertion and the tooth preparation attendant thereto.

The invention described herein addresses several of the most important concerns regarding the deficiencies of the Prior Art. The device disclosed herein has a unique structural concept which embodies strength and a conservative approach. The invention enables missing teeth to be replaced painlessly and expeditiously with fixed partial prosthodontics.

SUMMARY OF THE INVENTION

The principal object of the present invention is to replace teeth which are missing in a person's mouth by utilizing remaining teeth as anchoring mechanisms or abutments.

Another object of the present invention is to use these remaining teeth as abutments by preparing them in such a manner as to remove only minimal tooth structure.

Another object of the present invention is to fabricate these tooth replacements in such a manner as to cost much less than fixed partial dentures fabricated in the conventional manner.

These and other objects of the present invention are achieved by the mechanically retained fixed partial denture disclosed herein.

The mechanically retained fixed partial denture is comprised of three parts which, when placed together, lock onto abutment teeth and resist forces of displacement of the prosthesis in all directions.

To mechanical principle which forms the basis for this invention is the interlock. The interlock is defined as: to engage or interrelate with one another: lock into one another: interlace firmly; 1) to lock together: unite closely; 2) to connect in such a way that the motion of any part is constrained by another part: to arrange the connections of to ensure successive movement in proper sequence. (Webster's Third international Dictionary—Unabridged, Merriam-Webster Inc. 1986, U.S.A.)

This invention utilizes the interlock principle to engage and interrelate the three parts of the invention, to lock them into one another, united closely; and connected in such a way that the motion of any part is constrained by another part; and further, the connections of the device are so arranged that it can only be assembled or disassembled in the proper sequence.

The three parts of the invention are: a) a buccal element which is placed onto the abutment teeth from the buccal side, and utilizing retentive elements placed buccal to the buccal line angles of the abutment teeth, thus preventing lingual displacement; b) a lingual element which is placed onto the abutment teeth from the lingual side, and utilizing retentive elements placed lingual to the lingual line angles of the abutment teeth thus preventing buccal displacement; additionally, these retentive elements are placed within grooves cut into the tooth in a horizontal direction thus preventing superior and inferior displacement; and c) an incisal attachment element which comprises horizontal and vertical components so fabricated as to fit closely over the aforementioned buccal element and lingual element when the three elements are in close proximity.

Furthermore, the buccal element comprises a projection so fabricated as to fit within the body of the lingual element; the lingual element comprises an indentation so fabricated as to accept the same projection from the buccal element; both the same projection and the same indentation comprising a longitudinal aperture within them which are so matched as to provide a continuous longitudinal aperture extending through both simultaneously. Finally, the incisal attachment element comprises an elongated structure which extends from the inferior surface of the horizontal component of that element so as to pass through the aforementioned continuous longitudinal aperture of both the indentation and the projection when the three parts are closely opposed and fitted. This is the last step in the assembly of the device, and the device cannot be fully assembled unless the sequence of assembly includes this same last step. Conversely, the device may not be disassembled unless removing the incisal attachment element is the first step in the disassembly.

The three part structure, when fully assembled, will completely fill the space between two teeth, closely approximating both the mesial surface of the distal abutment and the distal surface of the mesial abutment. It can therefore be appreciated that there is no movement possible for each of the three aforementioned elements once they are engaged upon the tooth by the retentive elements, and the elongated structure from the incisal attachment element extends through both the lingual element and the buccal element, thus connecting all three elements in a mechanically interlocked system. Dental porcelain simulating the appearance and function of the natural teeth will be placed upon the incisal attachment element prior to final assembly. Thus the principle object of the invention is fulfilled.

One object of the invention is to place the grooves in as shallow a position as possible upon the teeth to avoid entering the dentin. The grooves for the retentive elements are prepared by a dental bur, appropriate for the thickness of enamel in that tooth to be prepared, which is held so that the long axis of the bur is held in the same plane as the long axis of the abutment tooth. The shape of the bur may vary according to tooth morphology or certain clinical situations, however, the bur must be of sufficient size to allow visible grooves following tooth preparation. The shank of the bur serves as a limiting mechanism to prevent deeper grooves than are necessary for the prosthesis. While holding the bur in this position, the operator will use the high speed turbine handpiece with water coolant to place a continuous groove extending from a point buccal to the buccal line angle of the abutment tooth into the interproximal region and thence to a point lingual to the lingual line angle of that same abutment tooth. These grooves will thus be nearly perpendicular to the long axis of the abutment teeth. The grooves on each of the abutment teeth will also be placed nearly parallel to each other.

Due to the latitude of accuracy afforded by this particular design it is possible to have grooves which are non-perpendicular to the long axes of the abutment teeth; and which are not exactly parallel to each other. This may be the situation when tooth position or rotation does not permit the ideal. However, the device can be so positioned as to accept many possible groove placements and still fulfill the requirements of the design.

Another object of this invention is to restore edentulous spaces with fixed partial prosthodontics in such a manner as to be far less expensive than the currently widely accepted methods. This is accomplished in the following manner:

a. The aforementioned three part device can be prefabricated industrially, such that the individual sizes and shapes of the various teeth, which are to be replaced, are readily available. Mass production techniques are far superior, in this regard, to the current method of having the dental laboratory technician fabricate, in wax, the tooth forms, which are then cast in metal using the lost wax technique. The standard fabrication of tooth forms or the "wax up" is time consuming, and may take several minutes to complete. In the preferred embodiment the three part device is prefabricated in acrylic resin (wax, plastic or any number of materials suitable for burnout and casting using the usual and standard lost wax technique are acceptable) and need only be minimally adjusted before insertion into the edentulous space, followed by addition of the retentive elements, and then casting. It is also possible to pre-cast this device in metal industrially, and add the retentive elements with solder, which decreases laboratory time even more. Thus a savings of many dollars, per unit, is realized.

b. Far more significant, in this regard, will be the time saved by the dentist. In the standard technique, the dentist must prepare the abutment teeth with a succession of burs, drilling, water spray and suction, to render the tooth in the correct form to accept the standard retainer. The tooth, thus prepared, must then be covered by a device known as the "provisional crown" to protect it from the oral environment. Additionally, the space between the teeth must be filled with an artificial tooth to prevent drifting of the teeth while the permanent bridge is fabricated. This is known as the "provisional bridge". The provisional crowns and bridges may require one half hour, or more to fabricate and cement upon the patient's teeth. The provisional prostheses often fall out, are uncomfortable, or unsightly, and may necessitate yet another visit to the dentist's office for correction.

For each tooth that must be prepared in this manner, there will be at least one hour of the dentist's time. Also, the fitting of the retainers, adjustments, and related procedures give a cumulative time effort of at least one and one half hours of dentist time per tooth prepared in the standard manner.

The invention will significantly reduce the dentist's time necessary to replace a missing tooth. The actual preparation of the teeth with the aforementioned grooves will take approximately one minute. The fitting and adjustments in the patient's mouth, after the dental laboratory has completed its phase of the procedure, will take only about ten minutes. Therefore it will be seen that the time savings of at least one hour and fifteen minutes will be realized for each tooth involved in the restorative procedure. Additionally, provisional crowns or bridges are unnecessary because the complete final prosthesis can be fabricated in just a few hours, ideally on the same day. It is anticipated that even more rapid reconstructions will be possible as the operator becomes familiar with the technique.

The cumulative time savings on the part of the dental laboratory and the dentist will result in a significant reduction in the fee that the patient will have to pay to receive this method of fixed partial dentures.

Although the present invention has been discussed in the context of replacing only single teeth with prefabricated tooth forms, it is to be appreciated that multiple teeth may be replaced as well. This is accomplished in the following manner:

a. Single units of the assembled three part device are luted together prior to casting by combining all of the buccal elements to each other; and combining all of the lingual elements to each other.

b. The incisal attachment elements are removed and cast separately.

c. The combined buccal elements are removed and cast together thus forming multiple combined buccal elements.

d. The combined lingual elements are removed and cast together thus forming multiple combined lingual elements.

e. After casting in metal the device is reassembled into the form that was established prior to casting.

d. The incisal attachment elements and their porcelain coverings are prepared singly, and inserted into their respective apertures.

Perhaps the most advantageous feature of this proposed invention is its conservative nature. Conservation of tooth structure is always preferable to removal of tooth structure when clinical circumstances permit. This proposed invention will markedly decrease the amount of tooth structure which would otherwise be lost in the conventional preparation. Also, the grooves placed in the tooth for the retentive elements are located far above the gum line, which allows for easy inspection for caries. Conversely, in the conventional preparation, the margin of the preparation is the usual place for caries to begin, and often this area is very difficult to inspect as it is usually at or below the gumline.

This invention eliminates many of the problems associated with conventional fixed partial prosthodontics. The procedures necessary to fabricate the mechanically retained bridge save time and effort for the laboratory technician and for the dentist. The amount of tooth structure that must be removed for the mechanically retained bridge is far less than tha necessary for conventional fixed partial prosthodontics. Additionally, there is a much larger chance of new tooth decay associated with the conventional techniques than with the mechanically retained bridge. The patient needs no injection of anesthesia and the complications of tooth preparation are obviated.

DETAILED DESCRIPTION OF THE INVENTION

Figure 1:
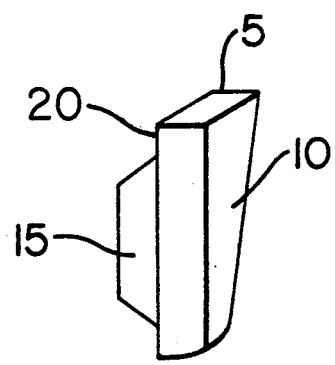
FIG. 1 shows the buccal element from the side view with the projection located on the inner surface.
Figure 2:
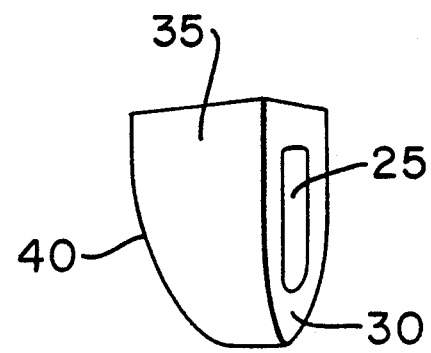
FIG. 2 shows the lingual element shown from the side with the indentation visible on the buccal surface.
Figure 3:
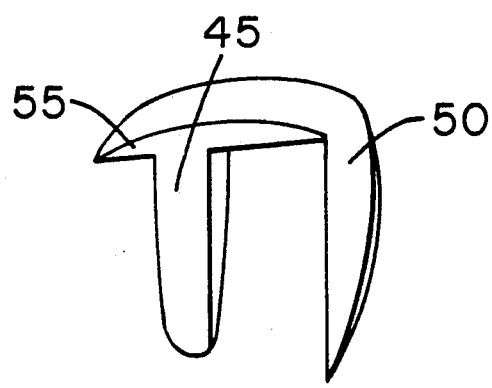
FIG. 3 shows the incisal attachment element from the side and its elongated member.
Figure 6:
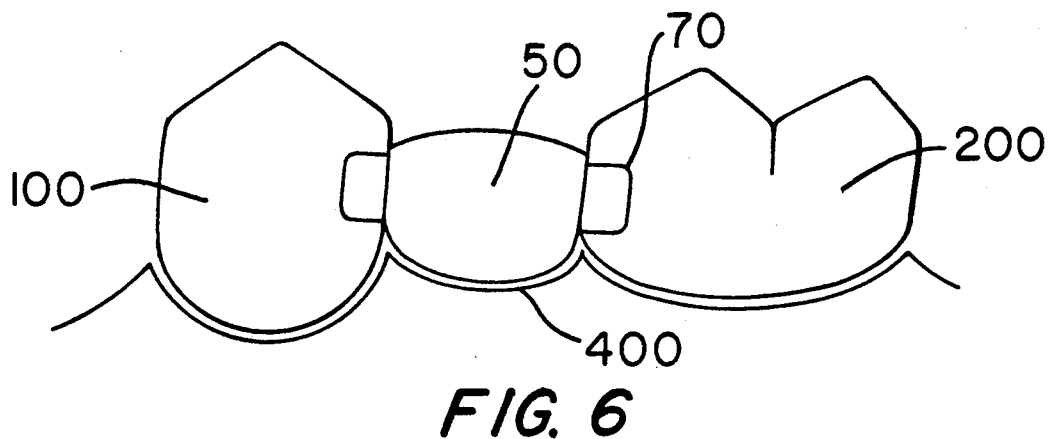
FIG. 6 illustrates the preferred embodiment of the invention positioned between two abutment teeth as shown from the buccal side.

Refer now to FIGS. 1,2,3 which are overall drawings of the invention in the unassembled phase. In the preferred embodiment as in FIG. 1 the buccal element 5 is the part of the three-part device which will be located toward the buccal side of the teeth. It comprises: the outer face 10 which is the buccal surface, and a projection 15 which is located upon an inner planar surface 20. Projection 15 further comprises an aperture passing therethrough best seen in FIG. 4 at 60. The inferior surface of the buccal element 5 is contoured to abut the gingival surface upon which it rests, as illustrated in FIG. 6 at 400.

Figure 7:
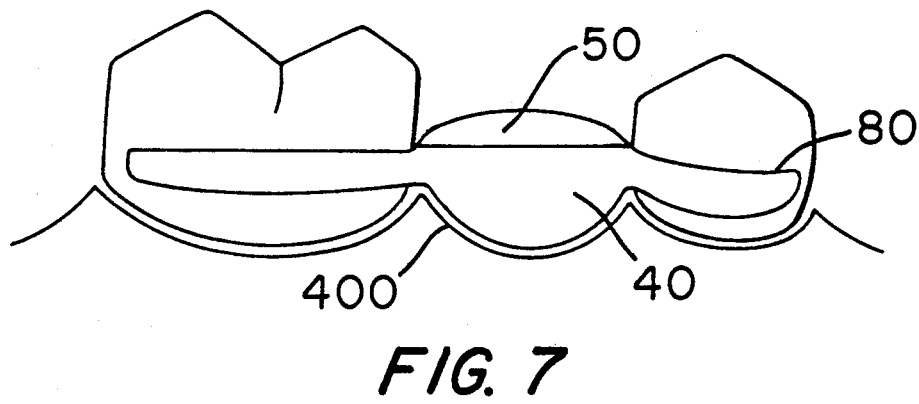
FIG. 7 illustrates the preferred embodiment of the invention positioned between two abutment teeth as seen from the lingual side.

FIG. 2 shows the lingual element 35 which is contoured on the lingual side 40 to conform to the lingual contours of the abutment teeth, whereas the inferior surface is contoured to abut the gingival surface upon which it rests, as illustrated in FIG. 7 at 400.

The buccal surface 30 of the lingual element 35 and the inner face 20 of the buccal element 5 are shaped and contoured such that when placed upon one another during assembly there is no discrepancy, void or irregularity between the two elements. The indentation 25 is so formed in size and shape as to accept, without hindrance, projection 15 when the buccal element 5 and lingual element 35, as depicted in FIGS. 1 and 2 respectively, are closely opposed and fitted.

FIG. 3 shows the incisal attachment element 50 from the side, with the elongated member 45 extending in a vertical direction from the inferior horizontal surface 55.

Figure 4:
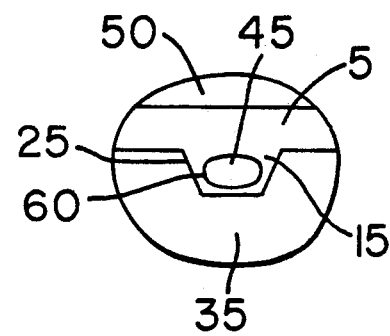
FIG. 4 is a cross-section through the middle of the assembled invention before attachment of the retentive elements.
Figure 5:
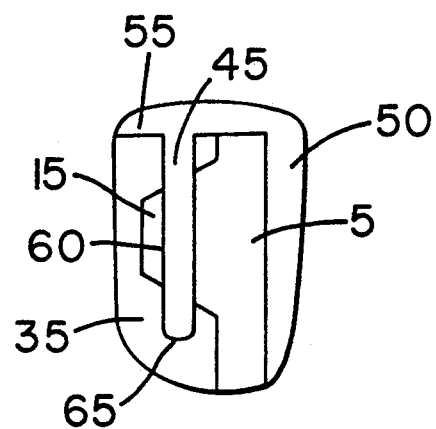
FIG. 5 is a sagittal section through the assembled invention at its midline.

FIG. 4 shows a cross section through the middle of the invention, when assembled, prior to the addition of the retentive elements. As will be appreciated, projection 15 fits within indentation 25. Aperture 60 extends from the superior surface of the lingual element 35 to within the body of that element, through the aperture in indentation 156, and then ends within the body of lingual element 35 at a point below the level of projection 15. In the preferred embodiment, upon assembly, the elongated member 45 extends, in a continuous manner, through the length of aperture 60. Thus, the elongated member 45 is seen within the aperture 60.

the mechanical arrangement of the linear aperture 670, extending through both the buccal and lingual elements simultaneously, is further illustrated FIG. 5 which is a sagittal section of the assembled device at its midline. This is the concept upon which this invention is based, for, when the elongated member 45, which extends vertically from the inferior horizontal surface 55 of the incisal attachment element 50, passes through this aperture 60, when the device is assembled, there is created an interlocking of the three parts of this device. The elongated member 45 ends at the point 65 in the preferred embodiment. Thus the three elements are mechanically fused to the extent that they are functionally one unit. Each of the three elements 5, 35, and 50 are united closely and interlaced together. According to the aforementioned definition they are interlocked.

Figure 8:
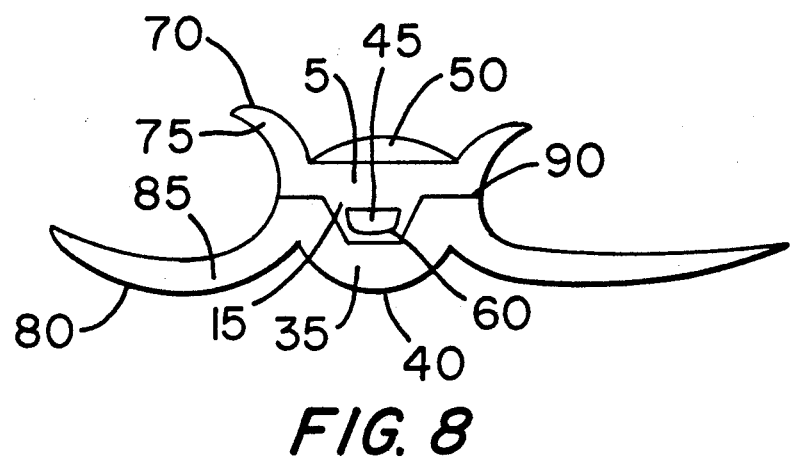
FIG. 8 is a cross sectional view through the middle of the preferred embodiment where the retentive elements are attached to the buccal and lingual elements.
Figure 9:
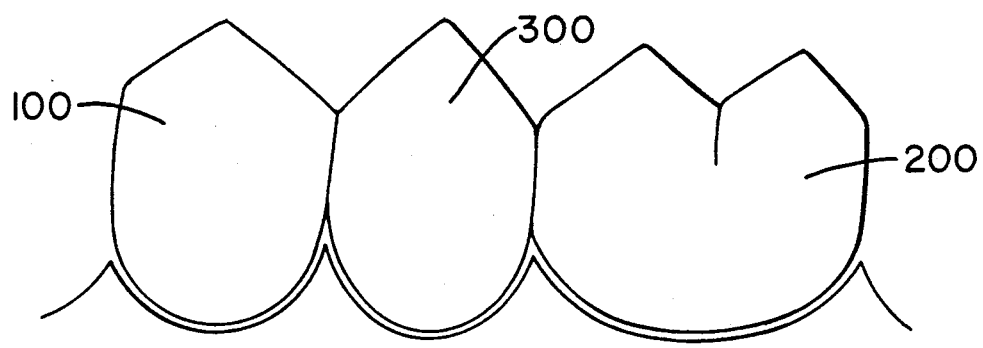
FIG. 9 illustrates the preferred embodiment where the finished tooth replacement is viewed from the buccal side.
Figure 10:
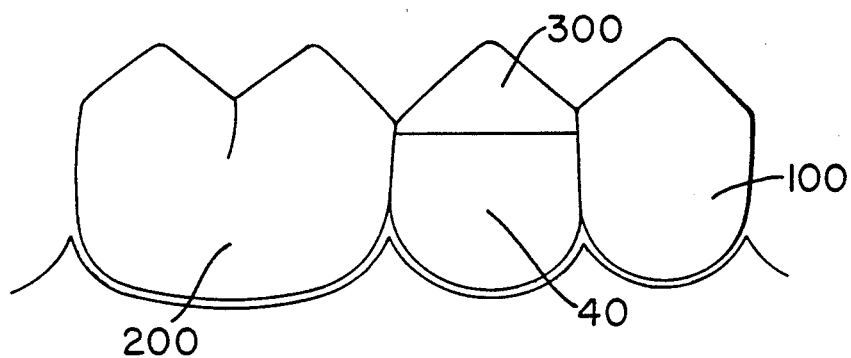
FIG. 10 shows the preferred embodiment where the finished tooth replacement is viewed from the lingual side.

This design is adaptable to any tooth morphology, in terms of height, width or depth. The preferred embodiment is the placement of this device as a pontic(s) in a fixed partial denture. This is accomplished as follows:

a. The dentist prepares the abutment teeth within the patient's mouth, without anesthesia, using the appropriate instruments, especially including a bur which will, when held against the long axis of the tooth, place a groove that will lie within the tooth to a depth that it is only within the enamel. Of course, the size of that bur will vary, based upon the tooth that is to be prepared. The grooves are prepared as close to parallel to one another, and as close to perpendicular to the long axis of the tooth, as is possible by the operator. The groove will extend from buccal to the buccal line angle of the tooth, which will place it upon the facial surface of the tooth; thence into the interproximal area; thence lingual to the lingual line angle of the tooth, which will place the groove upon the lingual surface of the tooth. The outlines of those grooves are illustrated by 70 in FIG. 6 which is the buccal view of the device (part 50 visible) positioned between the abutment teeth 100 and 200; and groove 80 as seen in FIG. 7, which is the lingual view of the device. The lingual surface of the lingual element 40 is visible in this illustration as well as is 50.

b. The dentist makes an impression of the teeth after this preparation, in the standard manner, and sends it to the dental laboratory. The dental technician prepares a model of this impression and then selects a prefabricated, assembled device which is the proper size and shape for that particular tooth which is to be replaced. The technician then contours the inferior surface of the device and positions it into the space by means of affixing it to the underlying gingival surface. It must be noted here that in the preferred embodiment, the device will be made of a solid dental material suitable for investment, burnout and casting such as acrylic resin. Other dental materials suitable for investment, burnout and casting are also possible. In the preferred embodiment, and for purposes of description, the device at this stage is fabricated in acrylic resin.

c. The technician then flows a labile material such as acrylic resin into the grooves and from thence to the device. Thus it will be appreciated in FIG. 8, which is a cross-section through the middle of the assembled device attached to the acrylic resin within the grooves, that the buccal element 5 and the acrylic resin within groove 70 have become one contiguous unit as depicted by 75. Similarly, it will be appreciated that lingual element 35 has become one contiguous unit with the acrylic resin within groove so as depicted by 85. Of course grooves 70 and 80 have matching opposite grooves on the other abutment tooth. There is a thin sheet of a separating material extending from between elements 5 and 35 that extends to also separate the acrylic resin in grooves 70 and 80. This is illustrated by 90.

d. The technician then separates the device by removing, first, the incisal attachment element 50, then the buccal element 5 and the lingual element 35 with their attached acrylic resin retentive elements 75 and 85 respectively. It should be noted here that, although not noted in the figures, there may be a "removal button" attached to any or all of the aforementioned elements to facilitate handling, as is standard practice in many dental laboratories. These elements are then separately invested, burnt out and cast into metal in the standard and accepted manner.

e. The technician finishes the castings in the normal manner and then reassembles the device upon the abutment teeth upon the model. In the preferred embodiment the reassembled casting is so accurate that the pieces fit together tightly enough so that cement is unnecessary. The friction of the combined elements is sufficient for retention.

f. In the preferred embodiment the incisal attachment element 50 is to be covered with dental porcelain that will simulate the natural anatomy, esthetics and occlusal function of the natural tooth that was missing. The dental porcelain is fused to the incisal attachment element 50 in the standard manner with an opaque base underlying the porcelain.

g. The technician returns the finished assembled device with the porcelain in place to the dentist who then affixes the device to the patient's abutment teeth in the mouth and examines the device for accuracy in every detail according to the proper and accepted principles of dentistry. In the preferred embodiment the now metal retentive elements 75 and 85 are opaqued on their outermost surface with a composite opaquer and then covered with a composite resin restorative material to completely cover those elements such that the device is not visible from the buccal side as illustrated in FIG. 9. This procedure of covering exposed metal, for esthetics, with composite opaquer and restorative materials is well known in the art. The porcelain covering the incisal attachment element 50 is illustrated by 300. FIG. 10 illustrates the lingual side in the preferred embodiment where the lingual surface 40 is visible as well as the porcelain 300. Thus it will be appreciated that the prefabricated device combined with the added retentive elements forms a very effective method of restoring the edentulous space in the dentulous arch.

Figure 11:
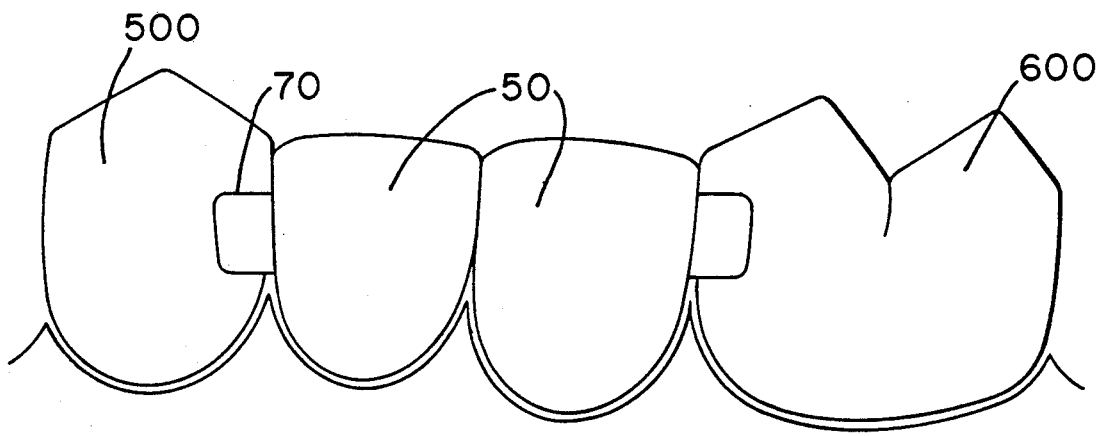
FIG. 11 illustrates the variation where the invention is adapted to replace more than one tooth in the arch as viewed from the buccal side.

The above description is the preferred embodiment of this invention, but there are many variations possible. For example, the device is adaptable for the restoration of more than one tooth. In FIG. 11 two of the assembled devices are shown placed between abutment teeth 500 and 600. The incisal attachment element 50 is illustrated on two adjacent teeth as shown from the buccal side. The groove outline 70 is visible. This arrangement is possible when the individual units are joined together with acrylic resin or other suitable material prior to casting in metal. The prosthesis is cast in metal and then finished with the porcelain and composite resin as in the case of the aforementioned individual tooth replacement situations.

Another variation is to make the entire prosthesis in metal without porcelain. In this case the superior surface of the incisal attachment element 50 would be contoured prior to casting to simulate in form and function the occlusal surface of the tooth that is to be replaced. After casting there would therefore be a metal occlusal surface, which is acceptable in the art and science of dentistry. The retentive elements would be covered with opaque and composite resin restorative material at the discretion of the operator and the patient.

Yet another variation is to cement the finished device together, and to the abutment teeth with an accepted dental cement. Although the device in the preferred embodiment is designed to stay affixed to the teeth without cementation, it will e appreciated that cementing the finished device to the abutment teeth will result in an extremely stable restoration. The cementing media and procedures are standard aspects of the practice of dentistry.

In summary, the invention is designed to fasten onto the abutment teeth from the buccal and lingual sides of those teeth. This invention comprises three parts: the buccal element, the lingual element, and the incisal attachment element. There are retentive elements attached to both the buccal element and the lingual element respectively. These retentive elements prevent movement of the device by engaging grooves placed within the butment teeth. The principle supporting the invention is an interlocking of the buccal element, the lingual element and the incisal attachment element by means of an elongated member that extends from the incisal attachment element through both the buccal element and the lingual element simultaneously to form a unitary functional unit. The occlusal surface of this invention is contoured to follow the proper functional patterns of the detention either by covering the incisal attachment element in porcelain or by creating the occlusal pattern in a labile material prior to casting, thus creating the occlusion in metal. The latter two procedures are standard techniques in the art.

The invention can be seen to fulfill the objects aforesaid the and advantages among others by replacing missing teeth in the mouth utilizing remaining teeth as anchoring mechanisms. Another object is fulfilled because the preparation of those teeth requires the removal of minimal tooth structure as compared to the standard methodology. Another object is fulfilled because the present invention utilizes prefabrication technology to decrease the time, effort, and expense necessary to replace missing teeth.

The foregoing description of the preferred embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the appended claims which should be broadly construed and should not be limited by their literal terms.

I claim:

1. A devices for restoring edentulous space in the dentulous aroh comprising:
   a. a buccal element comprising a superior surface which intersects at the superior buccal aspect with a buccal surface, said buccal surface facing toward the buccal direction; said superior surface intersects at the superior lingual aspect with a lingual surface, said lingual surface facing toward the lingual direction; the inferior surface of said buccal element contoured to abut the underlying gingival surface; said lingual surface of said buccal element further comprises a projection which has an aperture within said projection;
   b. a lingual element comprising a superior surface which further comprises an aperture; said superior surface intersects at the superior lingual aspect with a lingual surface, said lingual surface facing toward the lingual direction; said superior surface of said lingual element intersecting at the superior buccal aspect with a buccal surface, said buccal surface facing toward the buccal direction; said buccal surface further comprising an indentation; said indentation further comprising an aperture which is continuous with said aperture comprising said superior surface; the inferior surface of said lingual element contoured to abut the underlying gingival surface; and
   c. an incisal attachment element comprising a superior surface which intersects at the superior buccal aspect with the buccal surface of said incisal attachment element; said incisal attachment element further comprising an inferior surface located beneath said superior surface, said inferior surface intersecting at the superior buccal aspect with a lingual surface which is located lingual to said buccal surface of said incisal attachment element; said incisal attachment element further comprising an elongated member which extends from the said inferior surface of the said incisal attachment element in a vertical direction.

2. The device as claimed in claim 1 which further comprises retentive elements designed to engage abutment teeth by means where of:
   a. said buccal element comprises buccal retentive elements so contoured as to engage grooves cut into buccal surfaces and interproximal surfaces of said abutment teeth; said buccal retentive elements extending buccalward from both mesial and distal sides of said buccal element to buccal to the buccal line angles of said abutment teeth; said buccal retentive elements continuously engaging said grooves in such a manner whereby said buccal retentive elements prevent lingualward movement of said buccal element by means of engaging said abutment teeth buccalward to said buccal line angle, and said buccal retentive elements of said buccal element prevents superior and inferior movement of said buccal element by means of said engagement of said buccal and interproximal grooves of said abutment teeth; and
   b. said lingual element comprises lingual retentive elements so contoured as to engage grooves cut into lingual surfaces and interproximal surfaces of said abutment teeth; said lingual retentive elements extending lingualward from both mesial and distal sides of said lingual element to lingual to the lingual line angles of said abutment teeth; said lingual retentive elements continuously engaging said grooves in such a manner whereby said lingual retentive elements prevent buccalward movement of said lingual element by engaging said abutment teeth lingualward to said lingual line angle, and said lingual retentive elements of said lingual element prevents superior and inferior movement of said lingual element by means of said engagement of said lingual and interproximal grooves of said abutment teeth.

3. The device as claimed in claim 1 wherein said elongated member of said incisal attachment element passes through said aperture of said superior surface of said lingual element, thence through said aperture of said projection of said buccal element, and thence further into said aperture of said lingual element with said buccal element and said lingual element are closely opposed and interfitted.

4. The device as claimed in claim 1 wherein said device is fabricated in patterns specifically designed in size and contour to replace teeth in the mouth.

5. The device as claimed in claim 1 including means of combining individual units of said device into multiple units.

* * * * *